(12) United States Patent
Marquant et al.

(10) Patent No.: US 9,255,903 B2
(45) Date of Patent: Feb. 9, 2016

(54) METHODS OF PRODUCING AN ELECTROCHEMICAL SENSOR FOR DETERMINING AN ANALYTE CONCENTRATION

(71) Applicant: Roche Diabetes Care, Inc., Indianapolis, IN (US)

(72) Inventors: Michael Marquant, Mannheim (DE); Gregor Bainczyk, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/452,825

(22) Filed: Aug. 6, 2014

(65) Prior Publication Data

US 2014/0345130 A1 Nov. 27, 2014

Related U.S. Application Data

(60) Division of application No. 12/367,725, filed on Feb. 9, 2009, now Pat. No. 8,828,200, which is a continuation of application No. PCT/EP2007/058074, filed on Aug. 3, 2007.

(30) Foreign Application Priority Data

Aug. 8, 2006 (DE) .......................... 102006037328
Oct. 31, 2006 (EP) .................................... 06123227

(51) Int. Cl.
*G01N 27/327* (2006.01)
*A61B 5/145* (2006.01)
*A61B 5/1486* (2006.01)
(Continued)

(52) U.S. Cl.
CPC .......... *G01N 27/327* (2013.01); *A61B 5/14532* (2013.01); *A61B 5/14865* (2013.01); *C25D 5/48* (2013.01); *H01R 43/16* (2013.01); *Y10T 29/49204* (2015.01)

(58) Field of Classification Search
CPC .......... A61B 5/14532; A61B 5/14865; A61B 5/150274; G01N 27/327; C25D 5/48; Y10T 29/49204
See application file for complete search history.

(56) References Cited

U.S. PATENT DOCUMENTS

| 4,671,288 A | 6/1987 | Gough |
| 4,805,624 A | 2/1989 | Yao et al. |
| 5,286,362 A | 2/1994 | Hoenes et al. |

(Continued)

FOREIGN PATENT DOCUMENTS

| CA | 2050677 C | 3/1992 |
| DE | 4105222 A1 | 8/1992 |

(Continued)

*Primary Examiner* — Gurpreet Kaur
(74) *Attorney, Agent, or Firm* — Roche Diabetes Care, Inc.

(57) ABSTRACT

The invention relates to an electrochemical sensor for the determination of a concentration of at least one analyte in a medium, in particular a body tissue and/or a body fluid, to an apparatus that includes the electrochemical sensor, and to a use of the electrochemical sensor, and finally to a method for producing it. The electrochemical sensor has an isolation element and at least two electrodes. The at least two electrodes comprise at least one working electrode and at least one further electrode, in particular at least one counter electrode and/or at least one reference electrode. The at least two electrodes run parallel to one another and form an electrochemical measuring cell of the electrochemical sensor.

6 Claims, 5 Drawing Sheets

(51) Int. Cl.
*C25D 5/48* (2006.01)
*H01R 43/16* (2006.01)

(56) References Cited

U.S. PATENT DOCUMENTS

| | | |
|---|---|---|
| 5,591,139 A | 1/1997 | Lin et al. |
| 5,704,354 A | 1/1998 | Preidel et al. |
| 6,004,818 A | 12/1999 | Freilich et al. |
| 6,576,102 B1 | 6/2003 | Rappin et al. |
| 6,892,085 B2 | 5/2005 | McIvor et al. |
| 2005/0143635 A1 | 6/2005 | Kamath et al. |
| 2007/0093704 A1 | 4/2007 | Brister et al. |
| 2007/0197889 A1 | 8/2007 | Brister et al. |

FOREIGN PATENT DOCUMENTS

| | | |
|---|---|---|
| DE | 20009392 U1 | 11/2000 |
| EP | 0567725 A1 | 11/1993 |
| WO | 90/10861 A1 | 9/1990 |

Fig. 4.1

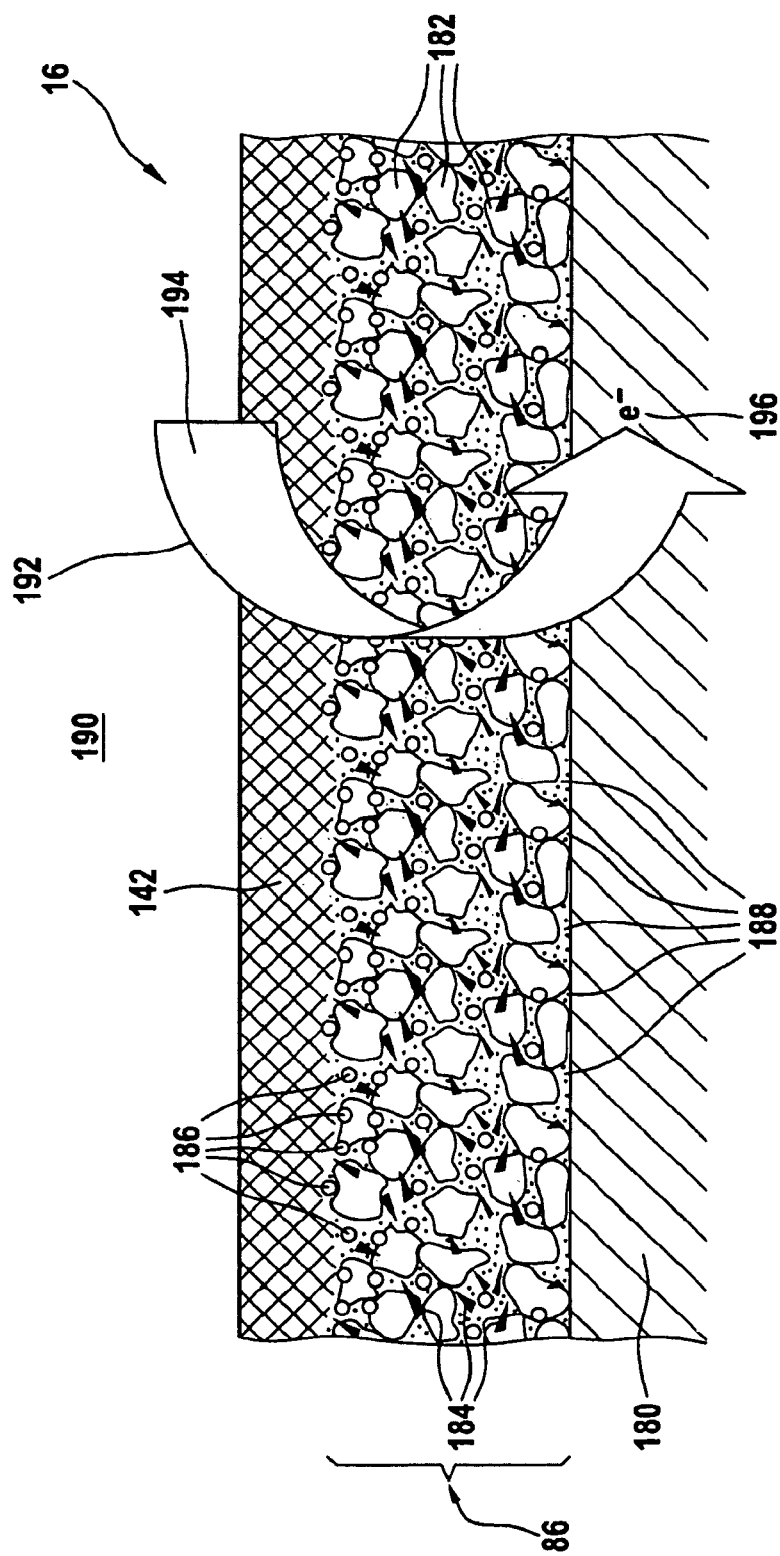

METHODS OF PRODUCING AN ELECTROCHEMICAL SENSOR FOR DETERMINING AN ANALYTE CONCENTRATION

CLAIM OF PRIORITY

This patent application is a divisional of U.S. patent application Ser. No. 12/367,725, (filed Feb. 9, 2009), which is a continuation based on and claiming priority to Int'l Patent Application No. PCT/EP2007/058074 (filed Aug. 3, 2007), which is based on and claims priority to DE Patent Application No. 102006037328.6 (filed Aug. 8, 2006) and EP Patent Application No. 06123227.8 (filed Oct. 31, 2006). Each patent application is incorporated herein by reference as if set forth in its entirety.

TECHNICAL FIELD OF THE INVENTION

The invention relates to an electrochemical sensor for the determination of a concentration of at least one analyte in a medium, in particular a body tissue and/or a body fluid, and further to an apparatus with which the electrochemical sensor is used, to a use of the electrochemical sensor and of the apparatus, and to a method for producing the electrochemical sensor. Such sensors or apparatuses are used, in particular, in the field of medical technology, for example in order to determine electrochemically a concentration of glucose (in particular blood glucose or glucose in a tissue fluid), lactate or other analytes, in particular metabolites.

BACKGROUND

The determination of the blood glucose concentration, and the corresponding medication is an essential item of the daily routine of diabetics. In this case, the blood glucose concentration needs to be determined quickly and easily several times a day, typically 2 to 7 times, in order to be able to take appropriate medical measures when relevant. In many instances, a modification is performed in this process by means of automatic systems, in particular with the aid of insulin pumps.

In order not to restrict the daily routine of the diabetic more than is absolutely necessary, use is frequently made of appropriately mobile units that should be easy to transport and to handle so that the blood glucose concentration can be measured without any problem, for example at the workplace or during free time.

There are currently available various mobile units that function in part according to different measuring methods and with the use of different diagnostic methods. A first measuring method is based, for example, on an electrochemical measuring method in which a blood sample that is taken from the body tissue of the patient by perforating a skin layer by means of a lancet is applied to an electrode coated with enzymes and mediators. Corresponding test strips for such electrochemical measuring methods are described, for example, in U.S. Pat. No. 5,286,362, the disclosure of which is hereby incorporated herein by reference in its entirety. Other known measuring methods use optical measuring methods that are based, for example, on the fact that the substance (analyte) to be detected can react with specific detection reagents, a change in color of the reaction mixture occurring in the process. Systems for detecting such color reactions and thus for detecting the corresponding analytes are known, for example from CA 2,050,677, the disclosure of which is hereby incorporated herein, by reference in its entirety.

The detection methods described are overwhelmingly based on the fact that a patient firstly takes an appropriate sample of the body fluid to be examined, this possibly being both a blood sample and a urine sample, this then being examined appropriately by means of the test apparatus. This method includes various disadvantages, however. Thus, this method is firstly extremely complicated and presupposes a number of handling steps. Thus, for example, a lancet needs to be provided and loaded, subsequently a skin layer must be perforated by means of this lancet, and then a blood drop thus produced must be applied to a test strip, and this test strip needs to be evaluated subsequently by means of an appropriate unit. For many patients, in particular older people and children, these handling steps can frequently be carried out only with difficulty, since the patients have restricted motor ability and limited eyesight, for example. Furthermore, these method steps can be carried out discretely only in a few instances so that, for example, protection of the privacy of the patient during a measurement at the workplace is only insufficiently preserved. Again, faulty operation in the course of the measuring method can easily lead to wrong measured values accompanied, in part, by fatal consequences of a false medication built on wrong measurement results.

For this reason, there are known from the prior art systems that generate continuously measured data and that can be used as an alternative or in addition to the above-described systems or methods, for example in order to reduce the number of individual measuring operations. Thus, for example, systems are commercially available that comprise a membrane tube in the subcutaneous tissue through which a transport liquid is pumped. Via the membrane, glucose diffuses into the transport liquid, which is then in turn conveyed to an electrochemical measuring cell. The glucose concentration is then measured in the electrochemical measuring cell. However, there is the disadvantage with such an arrangement for continuously producing measured values that it requires the patient to always carry along a supply of transport liquid and an appropriate waste container for holding contaminated transport liquid.

Further sensor types, known from the prior art, for continuously producing measured values are configured to be implanted in a body tissue; for example, U.S. Pat. No. 6,892,085 B2, the disclosure of which is hereby incorporated herein by reference in its entirety. Generally, such continuous monitoring set ups comprise an encapsulated glucose sensor system that comprises a glucose sensor and a protective capsule. In this case, three electrodes, a working electrode, a counter electrode and a reference electrode are provided that are applied to one side of a substrate. To improve implantability, this electrode arrangement can be integrated in a hollow needle that is used as an insertion aid to puncture body tissue. After the insertion, the hollow needles are withdrawn from the tissue again and only the sensors remain in the body tissue. Other exemplary systems are described, e.g., in U.S. Pat. No. 5,591,139, the disclosure of which is hereby incorporated herein by reference in its entirety.

A main advantage of the continuously measuring systems is that it is also possible to detect relatively short periodic fluctuations in the glucose concentration (time profiles) in conjunction with the intake of food and physical exercise. This is of great significance for "setting" of a diabetic.

The implantable sensors known from the prior art are, however, extremely complicated with regard to their design and production. If it is presupposed that these sensors are disposable sensors that can be used only for a short time (typically approximately one week), it then becomes clear that the methods used in the case of the sensors known from the prior art do not meet the requirements placed on disposable articles. Thus, for example, a complicated micro-structuring method, in particular a lithographic method, is required to produce the sensor known from U.S. Pat. No. 5,591,139. However, such methods cannot be combined with the production of cost-effective disposable articles. Again, complicated structuring methods are required to produce the sensor known from U.S. Pat. No. 6,892,085 B2, since the electrode pads must be structured carefully. In view of the small size of these electrodes, lithographic methods are likewise required therefor, and this in turn drives up the costs for producing such sensors.

Again, lithographic methods, in particular the etching of metal layers associated with these methods, are not always as reliable as is required for producing medical products. In particular, it can occur from time to time that individual electrodes are still interconnected by "bridges" or webs such that the functionality of the sensors can be slightly impaired or even completely negated, because of production problems. A further disadvantage of the sensors known from the prior art, such as are apparent from U.S. Pat. No. 6,892,085 B2 and U.S. Pat. No. 5,591,139, for example, consists in the use of a hollow needle or in the use of a capillary.

Instead of the previously described implantable sensors, in the case of which micro-structuring methods are used to structure the electrode pads, for example a lithographic method, implantable sensors, for example those known from WO 90/10861, the disclosure of which is hereby incorporated herein by reference in its entirety, can be formed in a wire-shaped fashion. That is, individual wires can be embedded in an isolating mass. The active measuring surfaces are respectively the end faces of the wires inside a plane that is exposed by a separating operation or the like. Such sensor systems are capable of multiple use, and can be used in an appropriate measuring instrument. The sample is applied inside the measuring instrument to the previously exposed end faces of the wires (in vitro measurement). Another example of systems employing wire-shaped sensors is disclosed in U.S. Pat. No. 4,805,624, the disclosure of which is hereby incorporated herein by reference in its entirety.

The above-discussed solutions in accordance with the prior art make contact with a body tissue only in a very restricted area. The electrode arrangement, usually comprising a working electrode, a counter electrode and a reference electrode, is very restricted locally, that is to say is capable of recording informative results only in a very small area of the body tissue. The functioning of the sensors known from the prior art, which can also be implanted, can be disturbed by local tissue inhomogeneities such as, for example, wound effects or fat deposits. Furthermore, sensor membrane characteristics can have a negative effect on the measured values. The electrode pads from other known systems have electrodes which lie next to one another in one plane and in the case of which the required miniaturizability is substantially restricted as a function of the selected micro-structuring methods. The disadvantage of the sensors known from the prior art, which can also be implanted, is to be seen in that it is impossible to make use of cost-effective production methods that are required for large batch production and could be used in the course of mass production.

SUMMARY

In accordance with the solution proposed according to the invention, an electrochemical sensor is proposed for the determination of a concentration of at least one analyte in a medium, in particular in a body tissue and/or a body fluid. The electrochemical sensor is generally configured in such a way that it can be implanted in a body tissue, and/or can be inserted subcutaneously. For this purpose, at least the exposed sensor surface is therefore configured to be biocompatible such that, in particular, no cytotoxins can diffuse into the body tissue, or come into contact with the body tissue.

The analyte can be, for example, glucose, lactate, hormones or other analytes that play a role in medicine, in particular. Alternatively, or in addition the electrochemical sensor can, however, also be used to measure other types of analytes. In particular, the sensor is based on the use of an electrochemical measuring method.

A basic idea of the invention consists in configuring the electrochemical sensor such that an arrangement of at least two thin wires forms an electrochemical measuring cell. The arrangement of thin wires simultaneously provides the electrical connection to a suitable measuring electronics. The measuring of the analyte concentration is then performed after the use of the electrochemical sensor by electrochemical (for example amperometric) measuring methods between the at least two electrodes—a working electrode and a counter electrode—particularly by means of a DC voltage. A reference electrode for currentless measurement of the working electrode potential can be used, in addition.

In order to achieve the most compact design possible for the electrochemical sensor, the individual electrodes of the electrode arrangement are aligned with one another, at least in one section, in substantially parallel fashion (that is to say an angular deviation of the parallel by not more than about 5° and even not more than 1°), and are generally isolated from one another by an isolation element. It is possible in this way to achieve more advantageous characteristics of the electrochemical sensor, because the sensor exhibits a typically good homogeneity along its longitudinal extent. In particular, the cell width of the sensor (that is to say thickness of the layers, electrode spacing etc.) exhibits a high uniformity and low tolerances.

The electrode arrangement generally comprises at least two electrodes, there being at least one working electrode and at least one further electrode, the at least one further electrode being intended to comprise one or both of at least one counter electrode and at least one reference electrode. In the case of the electrochemical sensor proposed according to the invention, the working electrode and the at least one further electrode are separated from one another by an isolation element. Alternatively or in addition, it is also possible for the electrodes to be embedded directly, completely or partly, in an isolation material. In the case of the electrochemical sensor proposed according to the invention, the isolation element of the electrochemically operating electrochemical sensor is represented by an electrically non-conducting material such as, for example, a plastic material.

Reference may be made to the following statements as regards the definition of the terms "isolation element" and "isolating". According to them, a direct contact of the electrodes with one another should be avoided. Of course, any isolation is only conditionally perfect, that is to say provided with an infinite resistance. Currents that do not flow through a transition between electrodes and electrolytes are generally denoted as leakage currents and corrupt the actual electrochemical measurement. Leakage currents are formed by the connected electronics, the plug and socket connection and in the sensor body itself. Leakage currents should generally be lower by a factor of one thousand than the actual sensor current.

The inventively proposed electrochemical sensor can be advantageously developed according to the invention in a very different way. The described advantageous developments can in this cast be used individually or in combination with one another.

Thus, the proposed electrochemical sensor can have at least one coating making electrical contact with at least the at least one working electrode. Whereas the at least one working electrode is typically produced from a material suitable for electrochemical purposes such as, for example, gold, silver, palladium, platinum or carbon, and the wire comprising the counter electrode can remain uncoated, and likewise be produced from a material made from one of the abovementioned materials suitable for electrochemical purposes. If a reference electrode is fashioned on the electrode arrangement of the inventively proposed electrochemical sensor, said reference electrode is typically an ion electrode of the second type that can be fashioned from a silver wire coated with silver chloride on its surface.

An electrode can be defined in this case as an interface between a first order conductor (charge transport by electrons in metal) and a second order conductor (charge transport by ions in an electrolyte). Use should generally not be made for the electrodes (first order conductor in contact with second order conductor) of any materials that passivate at the surface (form insulating oxide layers) such as, for example, aluminum. Working electrode and counter electrodes are redox electrodes, and so typically materials are chosen for electrodes comprising first order conductors that do not corrode or otherwise disintegrate in the event of polarization.

On account of the configuration of the at least one working electrode used and of the at least one counter electrode used, a slender design of the electrochemical sensor is possible for an inventive electrochemical sensor within the scope of the proposed electrode arrangement. This particular geometric shape enables the parallel placement of the at least one working electrode parallel to the at least one counter electrode, the result being to reduce substantially the action of the tissue inhomogeneities described at the beginning on the measurement result produced by the electrochemical sensor. Owing to the inventively proposed configuration of the electrode arrangement as three-dimensional geometry, the diameter of the sensor of compact design can be kept very small. The electrode surface required by the signal level can be provided on the basis of the peripheral surface of the electrode arrangement having at least one working electrode and at least one counter electrode.

In one embodiment, the proposed electrochemical sensor comprises three electrodes of wire-shaped formation that are isolated from one another by an isolation element using Y geometry. The isolation element using Y geometry is generally present as a plastic press-drawn section and can, as described below in even greater detail, be used in the course of large batch production when the inventively proposed electrochemical sensor is being produced. An isolation element using Y geometry provides the possibility of providing three holding compartments for holding the at least one working electrode, the at least one counter electrode and the reference electrode that is possibly used for measuring the working electrode potential. The plastic press-drawn section that is typically present using Y geometry and forms the isolation element lends the electrochemical sensor an adequate mechanical stability and tensile strength. This facilitates the handling of the electrochemical sensor not inconsiderably for unpractised users, as well. The sensor can be used, for example, together with an insertion aid (for example can be drawn under the skin with the aid of a needle, the needle being removed again). Thus, the sensor should have a certain tensile strength for this purpose. At the same time, however, it should be flexible so that upon deformation of the surrounding tissue (by movement or pressing on the skin) the sensor does not tear a wound in the tissue (some of which could result in the sensor supplying incorrect measured values, for example). These characteristics can be ensured by using the Y geometry.

The electrode arrangement of the proposed electrochemical sensor can be provided with a coating for immobilizing reactive components. This coating for immobilizing reactive components can be applied to the individual electrodes, that is to say at least one working electrode, the at least one counter electrode and, if appropriate, the at least one reference electrode or the finished electrode pack, which surrounds the isolation element. The electrode arrangement of the inventively proposed electrochemical sensor can comprise apart from the electrodes and the isolation element additional barrier layers that can, for example, be layers of a polymer, in particular an insulating polymer. Examples of suitable polymers are polyester, polyethylene, polypropylene or polyurethane. Other insulating polymers can also be used, it being possible to refer, in turn, to the above description with reference to the term "isolating".

The coating of the electrode pack with immobilization medium, or of the individual electrodes of the at least one working electrode, of the at least one counter electrode or the at least one reference electrode for immobilizing reactive components, can be a membrane layer that exhibits a partial permeability to the at least one analyte. The membrane layer can exhibit a permeability for glucose, lactate and/or further analytes to be detected. The membrane layer that can be used to coat the electrode pack or the individual electrodes mentioned should be impermeable to auxiliary chemicals used in the electrochemical measuring method, so that, for example, enzymes that are applied to one or more of the electrodes mentioned and partly exhibit a toxicity do not pass into the body tissue and do not contaminate the latter.

The membrane layer to be applied in order to immobilize reactive components that, for example, surround the electrode arrangement in the form of an envelope or enclose in the form of an envelope the individual electrodes of the electrode arrangement—the at least one working electrode, the at least one counter electrode and the at least one reference electrode. The applied coating of immobilization medium can, for example, have a polyurethane. A multilayer membrane layer structure is also possible. The coating of immobilization medium having, for example, a polyurethane can be applied here using a coating method such as, for example, an immersion method, a spray method, or an annular nozzle coating.

The configuration of the electrode arrangement for the electrochemical sensor can be performed in various ways. In particular, as described above, the at least two electrodes can comprise at least one working electrode and at least one further electrode that has at least one counter electrode and at least one reference electrode. In particular, the at least one counter electrode should be configured in such a way that the counter electrode enables an electrochemical redox reaction that permits a flow of current through the entire measuring cell. If, for example, an electrode reaction leads to electrons, the redox reaction at the respective other electrode should remove the corresponding number of electrons. The actual redox reactions can be completely independent of one another in this case. This redox reaction should typically not limit the current in such a way in this case that the detection reaction at the working electrode is no longer graduated over the entire concentration range (only two electrodes and an amperometric measuring method). In the case of a three electrode control with a fed-back reference electrode measuring section, the total cell voltage necessary for maintaining the counter electrode redox reaction should not overshoot the dynamic control range of the control electronics.

A counter electrode and a reference electrode can also be formed as a common electrode. The individual electrodes of the electrode arrangement can be coated with enzymes or other chemical auxiliaries that are respectively selected specifically as a function of the analyte to be detected. Thus, for example, in order to detect glucose it is possible to use glucose oxidase (GOD), which converts glucose into gluconolactone. The charge carvers thereby released are detected. In order to enable this detection, use is made of materials which reduce overvoltage and mediate charge, and that function rather like "charge mediators" between the medium and the electrodes. Materials that reduce overvoltage and mediate charge (such as manganese dioxide, for example) are also denoted as electrochemical redox catalysts.

Since the components of the on the detection reaction chain of the sensor can be dangerous for health, however, there is a need in many instances to immobilize these components in order to use an electrochemical sensor. For example, a covalent bonding to the electrode, and/or a layer of the electrode, for example a metal layer, can take place for the immobilization. This technique can be used, in particular to immobilize mediators. A further possibility consists in integrating the components wholly or partly in an insoluble layer that is insoluble in the fluid surrounding the electrochemical sensor in the implanted state, in particular the body fluid. It is also possible to use other types of redox mediators in common with respectively suitable enzymes for the specific detection of the respective analytes.

In addition to the configuration described for the at least one working electrode, it is also possible to configure the at least one reference electrode, and/or configure the at least one counter electrode in various ways. Thus, the at least one reference electrode should have an electrode system with an electrochemical potential that does not change, or changes only insubstantially, in a working range of the electrochemical sensor. Thus, for example, given a typical voltage load, i.e. a voltage between the working electrode and the reference electrode of typically no more than 400 mV, the electrochemical potential of the at least one reference electrode should generally change by not more than ±5 mV. It is ensured in this way that the reference electrode acts as true reference with whose potential the electrochemical potential of the at least one working electrode can be compared. In principle, it is possible to use suitable materials and/or material combinations for the reference electrode. A silver/silver chloride (Ag/AgCl) electrode system has proved to be particularly advantageous in this case. Other electrode systems can also be used in principle.

The at least one counter electrode of the proposed electrode arrangement for the inventively proposed electrochemical sensor can be configured in a multiplicity of various ways. In one embodiment, the at least one counter electrode is configured in a wire-shaped fashion in order to obtain a slender design of the electrode arrangement. However, it should be ensured in this case that the at least one counter electrode is configured in such a way that the at least one counter electrode enables an electrochemical redox reaction that permits a flow of current through the entire measuring cell. When an oxidation takes place at the at least one working electrode, a reduction should take place at the at least one counter electrode of the electrode arrangement, and vice versa. In principle, it is possible to use pure metals as counter electrodes such as, for example, platinum. However, this has the disadvantage that gas typically forms at such metal electrodes, for example hydrogen or oxygen forms. By way of example, gas forms in aqueous media at noble metals such as platinum when the redox reactions that are mandatory for the required transport of current can only be an electrolysis of water, that is to say there are in the electrolyte no sufficient concentrations of other redox-active species that can proceed within the potentials of the electrolysis of water. However, such a formation of gas is in some circumstances associated with difficulties in design, that is to say the design of the sensor must either be adapted to this formation of gas, or such a formation of gas must be avoided. To this extent, when an electrode system, in particular a redox electrode system, is used in the case of which the formation of gas is avoided, it is possible in this context to use the Ag/AgCl electrode system in an advantageous way. AgCl is reduced, for example, in this case. It may be seen in this that the at least one counter electrode is consumed during operation of the electrochemical sensor. If the at least one counter electrode has been consumed, gas frequently forms in turn, and so during operation the electrochemical sensor generally has a limited service life. Consequently, it is also advantageous when the at least one counter electrode of the proposed electrode arrangement is configured with a substantially larger actual electrode surface than the at least one working electrode of the electrode arrangement.

The proposed electrochemical sensor or an apparatus that includes such proposed electrochemical sensor is used generally for continuous determination of a concentration of at least one analyte in the body tissue and/or a body fluid. Here, "continuous" can be understood, for example, to mean that analyte concentrations are determined over a specific measurement period, for example one week, at regular intervals (thus, for example, every five minutes or every hour) or else permanently, that is to say with a temporal resolution that is limited only by the temporal resolution of a measuring instrument. However, during a continuous measurement there is a problem that over the measurement period the apparatus that comprises the inventively proposed electrochemical sensor can drift. A drift generally occurs when as a result of use the rate constant of one of the rate-determining steps in the entire reaction chain is varied. This can, for example, be a reducing enzyme activity, something which is, however, only the case as a rule when this determines the reaction rate. If possible, the enzyme should be dosed such that a buffer is present over the storage time and period of use. A change in the diffusion properties of a membrane during the period of use often has the strongest effect. A further problem is nonlinear dependencies of the measuring current on the glucose concentration, the function curve varying during storage times and periods of use. One of the rate-determining steps is then limiting here starting from a specific required turnover starting from a determining glucose concentration. Usually, a continuous measurement is performed by virtue of the fact that a "conventional" measuring method, for example the taking of a blood drop and measurement of the blood glucose concentration, is firstly used to carry out a reference measurement that is then compared with the measured value supplied by the implanted sensor. Subsequently, a measurement is performed over the measurement period on the basis of the initial reference measured value.

Furthermore, the invention proposes an apparatus for the determination of a concentration of at least one analyte in a medium, in particular a body tissue and/or a body fluid. The inventively proposed apparatus comprises at least one electrochemical sensor in accordance with the above description and possible refinements thereof. Furthermore, the at least one apparatus comprises at least one voltage measuring device for measuring a voltage of the at least one working electrode and the at least one reference electrode. Alternatively or in addition, at least one current measuring device can be provided for measuring a current between the at least one counter electrode and the at least one working electrode. In addition, the apparatus can comprise a control device which is configured in such a way that the current between the at least one counter electrode and the at least one working electrode is controlled in such a way that the voltage measured between the at least one working electrode and the at least one reference electrode is precisely equal to a prescribed desired voltage.

The described proposed electrochemical sensor can be used, for example, for a continuous determination of a concentration with the aid of at least one analyte in the body tissue and/or a body fluid. For this purpose, it is possible by way of example to implant the inventively proposed electrochemical sensor in the body tissue, for example as component of the inventive apparatus in one of the described configurations, doing so by puncturing. Subsequently, the sensor can be made available for a specific time within which at least an approximate equilibrium is set in the region of the sensor and the surrounding body tissue. Subsequently, the user can carry out a calibration measurement in the case of which, as described above, an analyte concentration in the body fluid, for example a glucose concentration in a blood drop, is determined by means of a conventional method. The data thereby determined are transmitted to the inventive apparatus, for example by manual input or by electronic data transmission, for example by means of a cable or by means of a wireless connection. A calibration point is thereby made available to the apparatus, and the inventive apparatus can offset the input measured values against measured values that are supplied by the implanted sensor. Subsequently, the implanted sensor and the inventive apparatus can be used, for example, over a period of a week, a measurement being performed, for example, every 5 minutes or else without interruption. The measured values determined by the inventive apparatus can, for example, be output to the patient, or they can also be made available to other systems, for example medication systems. Thus, the inventively proposed apparatus can be directly connected to an insulin pump that adapts an insulin dose to the measured blood glucose concentrations. Upon expiry of the measuring time, the complete apparatus can be exchanged, or it is also possible to exchange only the inventively proposed electrochemical sensor for a new, unused sensor.

It is also possible to implement a direction of data transmission that is reversed in relation to the above description. Thus, for example, the apparatus with implanted electrochemical sensor can be worn wholly or partly on the body. A calibration device can be provided separately to said apparatus or else as a component thereof (the inventive apparatus can be of multipart design) (for example as a separate hand unit), in order to undertake the described conventional calibration measurement (also denoted as "spot monitoring"). This calibration device can function, for example, as "master" unit to which the data determined with the aid of the implanted sensor are transmitted. It is then possible, for example, to provide a data memory, display elements and operating elements in the calibration device, and further evaluations of the measured data can be carried out.

Furthermore, a method is proposed for producing an electrochemical sensor, in particular an electrochemical sensor in accordance with the above description, which is suitable for the determination of an analyte concentration in a medium, in particular in body tissue and/or a body fluid. The method has the following steps, there not necessarily being a need to carry out the steps in the following sequence as quoted. Again, various method steps can be repeated and carried out in parallel, and it is possible to carry out additional method steps (not listed).

The production of the electrode arrangement for the inventively proposed electrochemical sensor can be performed by using effective, cost-effective production methods. In a first production step, the at least one working electrode of the inventively proposed electrode arrangement, which is typically produced from a material suitable for electrochemical purposes, such as, for example, gold, palladium, platinum and/or carbon, is coated with a reagent suitable for detecting the analyte. This can be performed during an annular nozzle coating, the annular nozzle that is used in the course of the annular nozzle coating and having a circular cross section enclosing at least one working electrode in annular fashion, and it being possible to carry out a coating of the entire peripheral surface of the at least one working electrode in one work operation. During this production step, the at least one working electrode forms a long endless wire that is advantageously capable of being coated on all sides and with a uniform film or coating thickness in the course of an annular nozzle coating. On completion of annular nozzle coating of the at least one working electrode, the at least one, coated working electrode traverses a drying station that is formed in one embodiment as a hollow cylinder, and so the at least one, coated working electrode traversing the drying station is uniformly dried.

The at least one, now coated working electrode, if appropriate the at least one reference electrode and, furthermore, the at least one counter electrode, which can remain uncoated, and can be produced from a material suitable for electrochemical purposes such as, for example, gold, silver, palladium, platinum or carbon, are assembled in a subsequent method step. In addition to said three electrodes of the electrode arrangement, the isolation element is also fashioned in the course of the assembly of the three said electrodes. The isolation element, which can have a Y or star geometry, for example, is in one embodiment an extruded section that is produced from plastic and, for example, by microextrusion. If, for example, an extruded section of Y geometry is used, three holding pockets advantageously result into which the at least one working electrode, the at least one counter electrode and the at least one reference electrode can be inserted.

An electrode arrangement is obtained in pack form after the assembly of the extruded section, that is to say the isolation element, and the at least one working electrode, the at least one counter electrode and the at least one reference electrode. In a subsequent production step, this electrode arrangement in the form of a pack can be fed through an immobilization medium coating in order to immobilize the reactive components in the course of a further processing operation configured in one embodiment as an annular nozzle coating method. The application of the immobilization medium coating in order to immobilize reactive components, which can be undertaken in one embodiment with the aid of an annular nozzle coating method for applying the immobilization medium coating in one work operation on the entire circumference in accordance with the electrode pack obtained in the previous work step, can also alternatively be executed at the individual electrodes, that is to say the at least one working electrode, the at least one counter electrode and the at least one reference electrode.

After the membrane coating method for applying a membrane in order to immobilize the reactive components, the electrode arrangement obtained in the form of a pack is fed to a cut-to-length operation. Cutting to length is understood below as the separation of the electrode pack that is present in endless form and provided with an immobilization medium coating, the electrode pack having the isolation element, which isolates from one another the at least one working electrode, the at least one counter electrode and the at least one reference electrode. The cutting to length of this electrode arrangement present in endless form is performed by cutting individual sections of the electrode arrangement in the form of a pack. Variable lengths can be separated in accordance with the cut-to-length operation, it being possible for one end of the electrode arrangement obtained, that is to say a section, to be mounted, for example, in a suitable insulation displacement connector. The other end of the separated section can be encapsulated in a positive locking part that also takes over other necessary functions of an electrochemical sensor such as, for example, insertion in the body tissue.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which:

FIG. 4.1 shows a section through the isolation element.

FIG. 9 shows a segment of a cross-sectional illustration of the surface of a working electrode.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
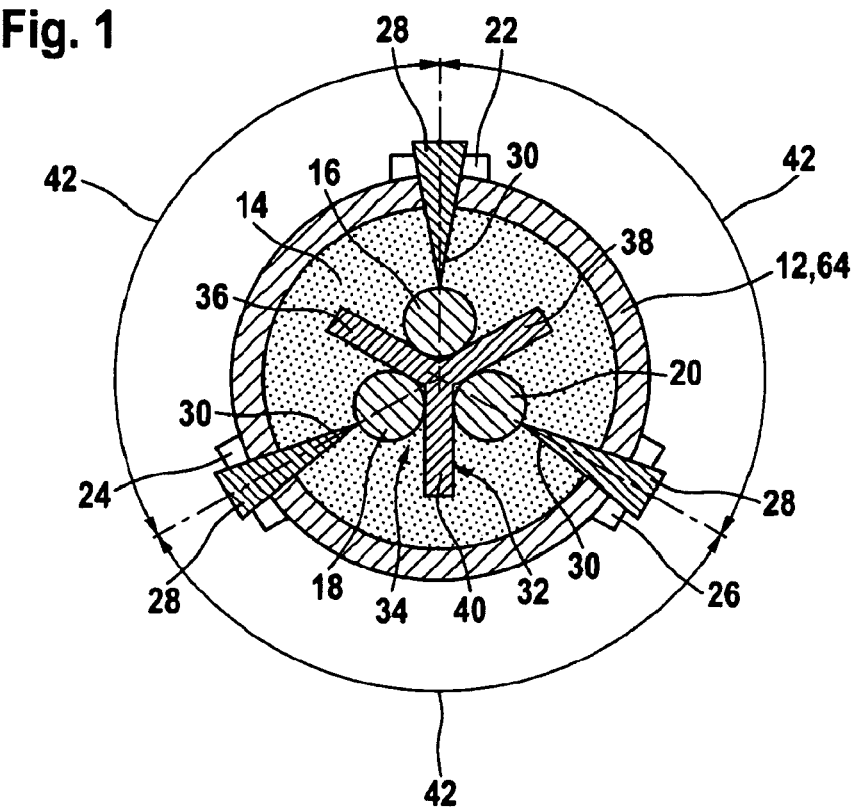
FIG. 1 shows a cross section through an insulation displacement connector for making electrical contact with the electrode arrangement of the disclosed electrochemical sensor.

The illustration in accordance with FIG. 1 is a section through a connector (designed in this example as insulation displacement connector) that comprises an electrode arrangement for an electrochemical sensor.

The cross section, illustrated in FIG. 1, through an electrochemical sensor 10 shows an electrode arrangement 16, 18, 20. The electrode arrangement 16, 18, 20 is surrounded by a sheath 12 that can enclose an embedding material 14. The electrode arrangement comprises at least one working electrode 16, at least one counter electrode 18 and at least one reference electrode 20. In the illustration in accordance with FIG. 1, the electrode arrangement 16, 18, 20 extends perpendicularly into the plane of the drawing, the at least one working electrode 16, the at least one counter electrode 18 and the at least one reference electrode 20 running parallel to one another.

The at least one working electrode 16, the at least one counter electrode 18 and the at least one reference electrode 20 form an electrochemical measuring cell and, at the same time, the body of the electrochemical sensor 10. The at least one working electrode 16 is produced from a material suitable for electrochemical purposes such as, for example, gold, silver, palladium, platinum or carbon. The use of further noble metals or other metals or metal alloys, including in multilayer arrangements, is also conceivable. The at least one working electrode 16 can be coated with a suitable reagent in order to detect the analyte, as is described in further detail below.

The at least one counter electrode 18 is likewise produced from a material suitable for electrochemical purposes such as, for example, gold, silver, palladium, platinum or carbon, and can remain uncoated, or else coated with one or multiple plies. In turn, as also in the case of the other electrodes, it is also possible here alternately or in addition to make use of further metals (such as noble metals) or metal alloys or multilayer metals. The at least one reference electrode 20 is produced in one embodiment from a silver wire that is coated on its peripheral surface with silver chloride. The at least one reference electrode 20 is used for currentless measurement of the potential of the at least one working electrode.

However, it emerges from the illustration in accordance with FIG. 1 that there is respectively formed on the circumference of the sheath 12 of the electrochemical sensor 10 a connection 22 for making electrical contact with the at least one working electrode 16, a connection 24 for making electrical contact with the at least one counter electrode 18, and an electrical connection 26 for making electrical contacts with the at least one reference electrode 20. In the illustration in accordance with FIG. 1, the number of connections 22, 24, 26 that corresponds to the number of electrodes 16, 18, 20 is arranged in a circumferential arrangement 42 that is 120° in the illustrated schematic reproduced exemplary embodiment. Depending on the number of the individual electrodes used on the electrode arrangement 16, 18, 20, a number of connections 22, 24, 26 that corresponds thereto is provided on the sheath 12 of the electrochemical sensor 10. In the case of the exemplary embodiment illustrated in FIG. 1, the at least one working electrode 16, the at least one counter electrode 18 and the at least one reference electrode 20 make electrical contact via contacting elements 28. The contacting elements 28 can be formed as insulation displacement connecting devices that comprise a cutting edge 30. A pointed end of the cutting edge 30 formed in wedge-like fashion on the contacting elements 28 respectively makes contact with the circumference of the at least one working electrode 16, the at least one counter electrode 18 and the at least one reference electrode 20. An alternative to an insulation displacement connector, it is also possible to expose the ends of the wires and solder, bond or glue them separately to a connection board.

By way of example, this arrangement can subsequently be encapsulated, for example in a connector housing.

It emerges, furthermore, from the sectional illustration in accordance with FIG. 1 that the at least one working electrode 16, the at least one counter electrode 18 and the at least one reference electrode 20 are isolated from one another by an isolation element 32. In the illustration in accordance with FIG. 1, the isolation element 32 is formed using a Y geometry, thus respectively yielding a holding compartment that holds the at least one working electrode 16, the at least one counter electrode 18 and the at least one reference electrode 20. The isolation element 32 is produced in one embodiment as an extruded section. Instead of the Y geometry 34 illustrated in FIG. 1, the isolation element 32 can also have another configuration, for example a design in a X-shaped or T-shaped fashion. A cross-shaped formation of the geometry of the isolation element 32 is also possible. It should be ensured that the geometry 34 of the isolation element makes sure that the at least one working electrode 16, the at least one counter electrode 18 and the at least one reference electrode 20, which run parallel to one another, are separated from one another by webs by the isolation element, for example by the isolation element 32.

The isolation element 32 illustrated in FIG. 1 in section with Y geometry 34 comprises a first web 36, which separates the at least one counter electrode 18 from the at least one working electrode 16. A second web 38 of the isolation element 32 separates the at least one working electrode 16 from the at least one reference electrode 20 that, in turn, is separated by a third web 40 of the isolation element 32 from the at least one counter electrode 18 of the electrode arrangement 16, 18, 20.

Figure 2:
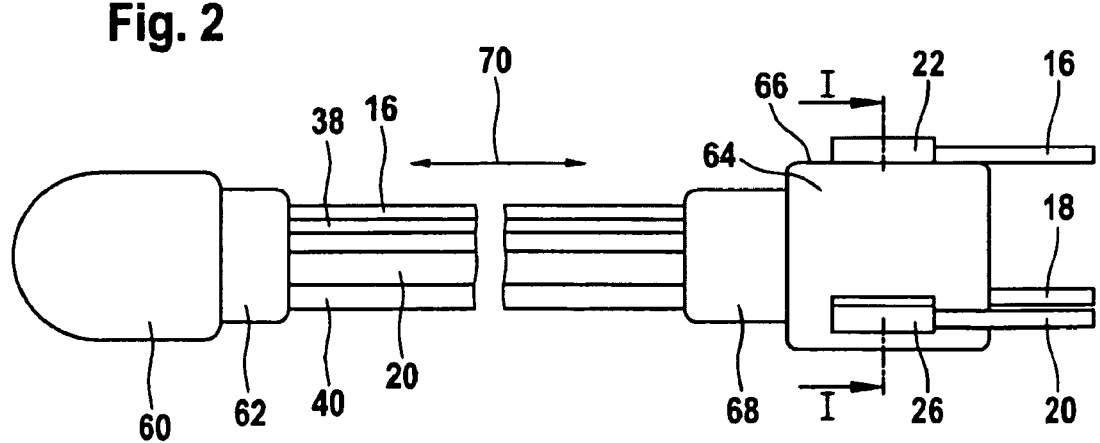
FIG. 2 shows a schematic side view of the proposed apparatus for the determination of an analyte concentration in a medium, with an insertion head and the insulation displacement connector.

An apparatus that includes the electrochemical sensor in accordance with FIG. 1 is illustrated in FIG. 2.

It may be gathered from the schematic illustration in accordance with FIG. 2 that the electrochemical sensor 10 is part of an apparatus that has an insertion head 60. The insertion head 60 is formed with a rounded end and in one embodiment has a diameter of <about 1 mm, in other embodiments has a diameter of <about 500 micrometers, and in yet other embodiments has a diameter of <about 50 micrometers. The insertion head 60 serves for the subcutaneous introduction of the electrochemical sensor into a body tissue. The insertion head 60 is sealed off from the electrode arrangement 16, 18, 20 via a first seal 32, only the at least one working electrode 16 and the at least one reference electrode 20 being, illustrated in the illustration in accordance with FIG. 2. The double-headed arrow denoted by the reference numeral 70 indicates the direction of movement in the apparatus for the determination of an analyte concentration in a body tissue or in a body fluid.

As an alternative to the method, illustrated in FIG. 2, for inserting by means of the insertion head 60, other apparatuses or modes of procedure for which no insertion head 60 is required are, however, also conceivable in order to insert the electrochemical sensor 10. Thus, for example, the electrochemical sensor 10 can be inserted into the tissue via a slotted hollow needle, it being possible instead of an insertion head 60 to make use only of an isolation of the end face of the sensor 10. Alternatively or in addition, the electrochemical sensor 10 can also be drawn under the skin by means of an insertion aid, for example a needle or a blade. In this case, it is possible for example to make use of a positive locking part that serves as a driver and does not also withdraw the electrochemical sensor 10 again upon withdrawal of the insertion aid. The electrochemical sensor 10 itself should, however, be configured in such a way that it can also be removed from a tissue again relatively easily at the end of its use.

Aside from the insertion head 60 and electrode arrangement 16, 18, 20, the apparatus illustrated in FIG. 2 comprises an adapter 64, illustrated in cross section in FIG. 1, that, as described above in conjunction with the exemplary embodiment of FIG. 1, can be formed as an insulation displacement connector. The adapter 64 ensures the electrical contact with the at least one working electrode 16, the at least one counter electrode 18 and the at least one reference electrode 20. The adapter 64 has a circumference 66 on which electrical contact is made with the connections 22, 24, 26, illustrated in FIG. 1, for making electrical contact with the at least one working electrode 16, the at least one counter electrode 18 and the at least one reference electrode 20. As already mentioned in conjunction with FIG. 1, the electrical contacting elements 28 can be formed as wedge-shaped elements which include cutting edges 30 and respectively make electrical contact with the circumferential surface of the at least one working electrode 16, the at least one counter electrode 18 and the at least one reference electrode 20. Moreover, the apparatus in accordance with the illustration in FIG. 2 comprises an evaluation unit that evaluates the signals which are transmitted via the at least one working electrode 16 and the at least one counter electrode 18, and undertakes a determination of the analyte concentration in the body tissue or in a body fluid and displays it directly to the user.

It may be mentioned for the sake of completeness that the course of the cut I-I corresponds to the cut, illustrated in FIG. 1, through the electrochemical sensor 10. A second seal 68 is located between the adapter 64, which can be designed as positive locking part, and the electrode arrangement 16, 18, 20. Depending on the cutting to length of the electrode arrangement 16, 18, 20, comprising at least one working electrode 16, at least one counter electrode 18 and at least one reference electrode 20, it is possible to implement different lengths of electrode arrangement 16, 18, 20 between the first seal 62, relating to the insertion head 60, and the second seal 68, relating to the adapter 64. It is possible in a fashion corresponding to the cutting to length of the electrode arrangement 16, 18, 20 to undertake a more or less deep subcutaneous insertion of the electrochemical sensor into a body tissue in order to determine an analyte concentration. In this case, following the inventive solution the at least one working electrode 16, the at least one working electrode 18 and the at least one reference electrode 20 form the electrochemical measuring cell, which is enclosed by the body tissue after insertion of the insertion head 60, and enables an analyte to be detected in a body tissue or a body fluid. Because of the formation of the at least one working electrode 16, the at least one counter electrode 18 and the at least one reference electrode 20 as wire-shaped components, the electrode arrangement 16, 18, 20 has a very elongated surface. Consequently, because of the high, elongated electrode surface the electrochemical detection takes place over a large tissue area. Consequently, local inhomogeneities (for example insulating fat cells) have a slight influence on the total current, since integration is performed over a relatively large area. A high current turnover is typically also associated with a high glucose consumption. This can lead in the tissue to instances of depletion, thus to measured values that are falsely determined as excessively low. The goal is therefore not to select the electrode surface, but at the same time to cover a great deal of space in the tissue. This goal is reached, in particular, by long, thin wires. Alternatively or in addition, the glucose consumption can also be choked by a thicker immobilization layer. The thinner the electrode pack is designed, the weaker as a rule are the disturbing interactions with the body tissue (for example cell growth or wound healing).

Figure 3:
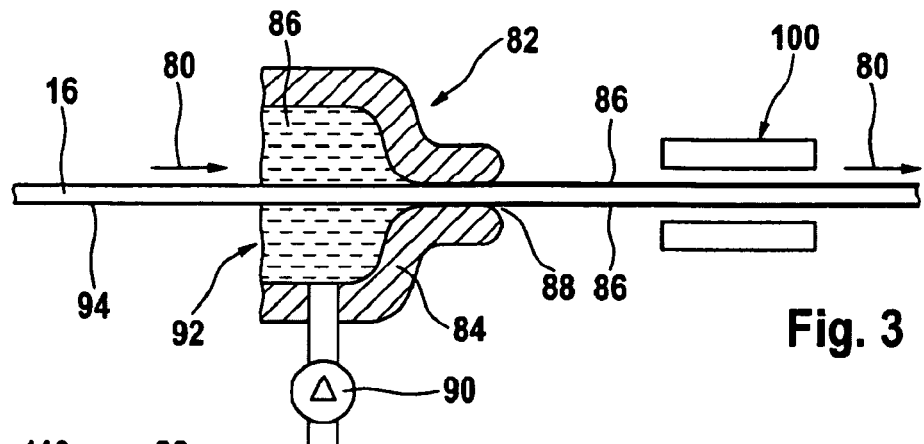
FIG. 3 shows an arrangement for coating an individual electrode of the electrode arrangement in order to apply a reagent medium suitable for detecting an analyte, with downstream drying station.

A first production step of the electrode configuration as illustrated in FIGS. 1 and 2 with the aid of an electrochemical sensor is to be gathered from the illustration in accordance with FIG. 3.

The inventively proposed electrochemical sensor 10 is distinguished by a production method that enables a use of individual production steps that are advantageous for large batch production. The components of the electrochemical sensor 10 are substantially the at least one working electrode 16, the at least one counter electrode 18 and the at least one reference electrode 20 and the isolation element 32. The production of a single ply or multiply coating of the at least one working electrode 16, the at least one counter electrode 18 and the at least one reference electrode 20 is described below in more detail.

In order to detect the analyte that is to be determined in a body tissue, the at least one working electrode 16 of the electrode arrangement 16, 18, 20 is coated with a reagent suitable therefor. In accordance with the illustration in FIG. 3, this coating step is undertaken in the course of an annular nozzle coating 82. For this purpose, the at least one working electrode 16 is moved through an annular nozzle 84 in the conveying direction 80. The annular nozzle 84 comprises a cavity 92 that is filled with a reagent medium 86. The conveyance of the reagent medium 86 into the cavity 92 of the annular nozzle 84 is performed by a feed pump 90. Owing to the fact that the reagent medium 86 is applied to the cavity 92 of the annular nozzle 84, the at least one working electrode 16, which is present in wire-shaped form, is coated with the reagent medium 86 in one work operation as the cavity 92 of the annular nozzle 84 passes in the conveying direction 80 by its surface 94. The reagent medium 86 can, for example, be a mixture of manganese dioxide (brownstone), graphite and GOD (glucose oxidase), which convert glucose catalytically into gluconolactone. The at least one working electrode 16, which leaves the annular nozzle 84 in the conveying direction 80, has a coated surface 94 formed by the reagent medium 86 after passing through an exit opening 88 of the annular nozzle 84. The film of the reagent medium 86 on the surface 94 of the at least one working electrode 16 is dried in a drying station 100 downstream of the annular nozzle 84 in the conveying direction 80 of the at least one working electrode 16 before the production steps described below follow on.

Figure 4:
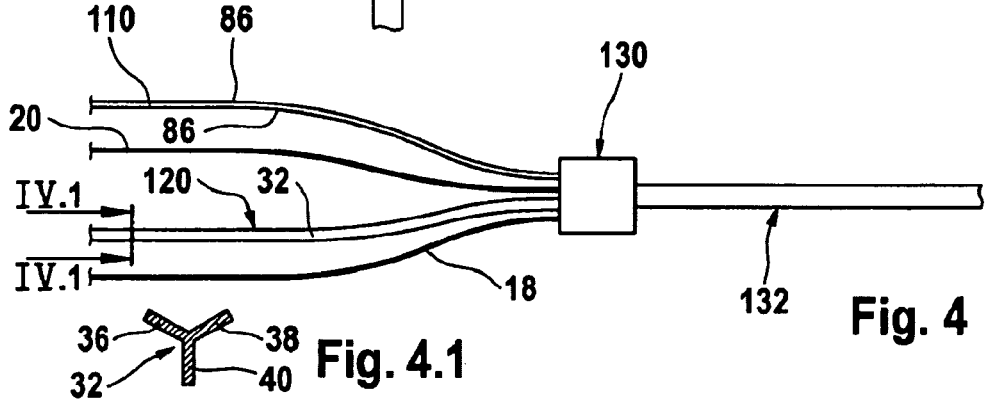
FIG. 4 shows the assembly of the at least one working electrode, the at least one counter electrode, an isolation element and a reference electrode to form an electrode arrangement.

FIG. 4 shows the assembly of the at least one coated working electrode with the at least one counter electrode, the at least one reference electrode and the isolation element present in slab form.

The at least one working electrode 16 coated with a reagent medium 86 in the course of the coating step 82 in accordance with the illustration in FIG. 3 is fed as at least one working electrode 110 to an assembly station 130. Furthermore, the assembly station 130 is fed the at least one, counter electrode 18 and the at least one reference electrode 20. Furthermore, the assembly station 130 is fed the isolation element 32, which is typically produced as an extruded section and in one embodiment has the Y geometry illustrated in FIG. 4.1. The now coated at least one working electrode 16, and the at least one uncoated or coated counter electrode 18 and the at least one reference electrode 20 are grouped around the isolation element 32 in the assembly station 130 such that the at least one working electrode 16, the at least one counter electrode 18 and the at least one reference electrode 20 are isolated from one another. The assembly station 130 leaves an electrode arrangement that comprises at least one coated working electrode 16, at least one counter electrode 18, at least one reference electrode 20 and the isolation element 32. The electrode arrangement 16, 18, 20 leaving the assembly station 130 constitutes an electrode pack 132.

Figure 5:
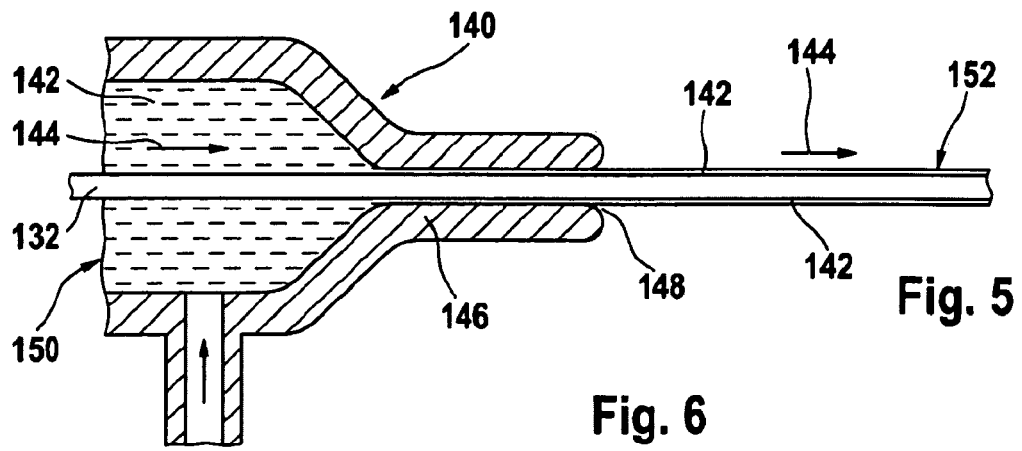
FIG. 5 shows an annular nozzle coating station for applying to the electrode arrangement a membrane that enables an immobilization of reactive components.

A further production step, which is fed the electrode pack in accordance with FIG. 4 after the assembly, is to be gathered from the illustration in accordance with FIG. 5. FIG. 5 shows that the electrode pack 132, which comprises the at least one coated working electrode 110, the at least one counter electrode 18 and the at least one reference electrode 20, is fed to an immobilization medium coating operation 140. In the course of the immobilization medium coating operation 140 illustrated in FIG. 5, an immobilization medium 142 is, for example, applied to the electrode pack 132 running into an annular nozzle 146 in accordance with the illustration in FIG. 5, in order to immobilize reactive components. As a result, the electrode pack is additionally isolated, and/or poisonous components (for example the GOD acting as cytotoxin) are prevented from diffusing into the body tissue. The outside of the electrochemical sensor 10, which comes into contact with the body tissue, should be biocompatible (that is to say not rejected by the body). That is a further beneficial characteristic of the immobilization medium 142. Alternatively or in addition, it is also possible to apply an additional layer that ensures this additional characteristic of biocompatibility. Again, the further materials used that come into contact with the body tissue, for example materials for isolation in the connector area and at the insertion end, should have corresponding biocompatible characteristics, or be appropriately coated.

The annular nozzle 146 used in the course of the immobilization medium coating operation 140 comprises a cavity 150 that has an exit opening 148 and is filled with an immobilization medium 142. The cavity 150 of the annular nozzle 146 is continuously filled with the immobilization medium 142, and so the entire surface of the electrode pack 132 running into the cavity in the conveying direction 80 is wetted by the immobilization medium 142. The peripheral surface of the electrode pack 132 that runs into the annular nozzle 146 in the conveying direction 80 is provided with a coating with immobilization medium 142 at the exit opening 148 of the annular nozzle 146. The conveying direction of the electrode pack 132 is denoted by reference numeral 144 in the illustration in accordance with FIG. 5. Reference numeral 152 denotes the electrode pack 132 coated with the immobilization medium 142.

Instead of the electrode pack 132 that enters the annular nozzle 146 in FIG. 5 in the conveying direction 144 and comprises the at least one working electrode 16, the at least one counter electrode 18 and the at least one reference electrode 20, which are isolated from one another by the isolation element 32, it is also possible for individual ones of the at least one working electrode 16, the at least one counter electrode 18 and the at least one reference electrode 20 to be fed to the immobilization medium coating operation 140. The immobilization medium coating 140, which can be applied in accordance with FIG. 5, makes the contact between the at least one coated working electrode 110 and the at least one counter electrode 18, and the body tissue or the body fluid, as a result of which the presence of a specific analyte is to be determined. A cutting to length step can be gathered from the illustration in accordance with FIG. 6.

Figure 6:
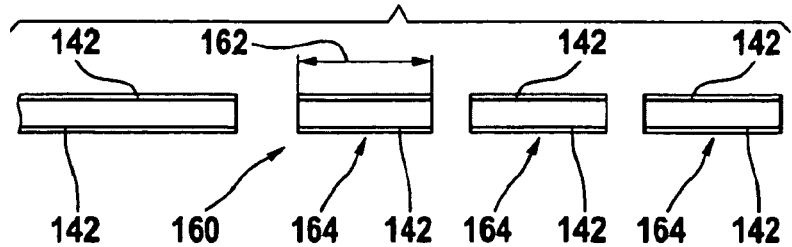
FIG. 6 shows a cut-to-length operation of the electrode arrangement provided with an immobilization medium coating.

In accordance with the cutting to length operation 160 illustrated schematically in FIG. 6, the coated electrode pack 152, which is provided in accordance with the preceding production steps and is coated on the circumference, for example, with the immobilization medium 142, is cut to length into individual sections 164. The cutting to length operation 160 is typically performed by transverse cutting of the coated electrode pack 152. It is possible in this process to set different lengths 162 of the cut-to-length sections 164 depending on the purpose of application.

The insertion head 60, illustrated in FIG. 2, together with the first seal 62 is fastened at one end to the sections 164 produced in accordance with the cutting to length operation 160, and the connection board 64 illustrated in FIG. 2 and to which the connections 22, 24, 26 are connected in accordance with the number of the electrodes of the electrode pack 132, is fastened at the other end. This produces the apparatus (not illustrated to its entire length in FIG. 2) that comprises an electrochemical sensor 10. The electrochemical measuring cell of the electrochemical sensor 10 is formed by the peripheral surface of the layer, applied in the course of the immobilization medium coating operation 140, of the immobilization medium 142. This layer made from immobilization medium 142 constitutes the boundary of the electrochemical measuring cell, and the contact surface with the aid of which the electrochemical sensor 10 makes contact with the body tissue or the body fluid.

Figure 7:
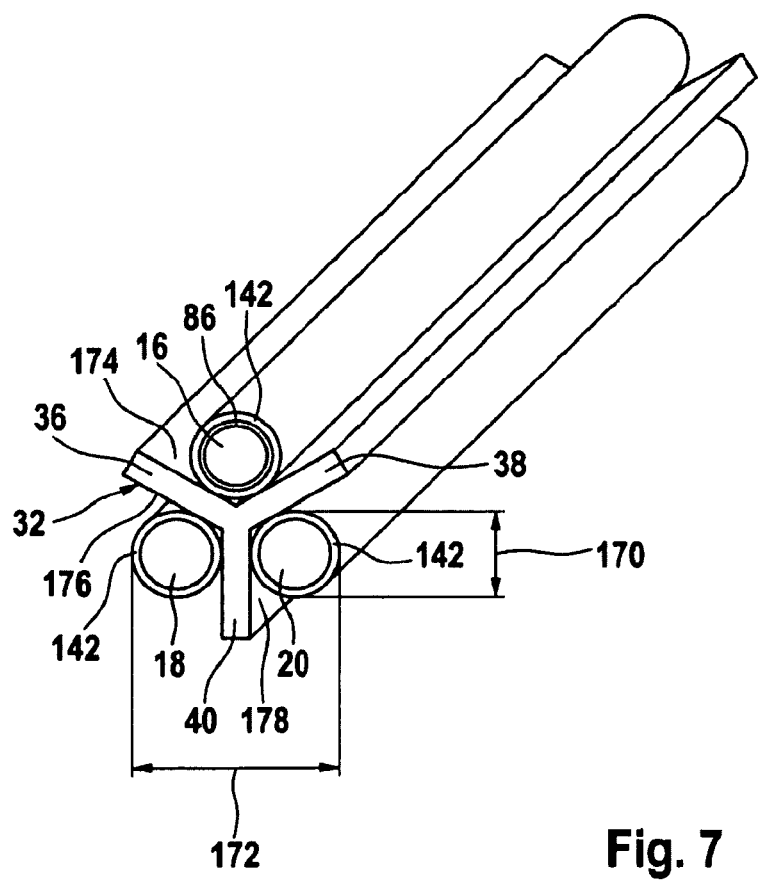
FIG. 7 shows a perspective plan view of the inventively proposed electrode arrangement.

A perspective view of the electrode arrangement of the electrochemical sensor 10 is to be gathered from the illustration in accordance with FIG. 7.

It emerges from the illustration in accordance with FIG. 7 that the at least one working electrode 16, the at least one counter electrode 18 and the at least one reference electrode 20 are separated from one another via the isolation element 32. The isolation element 32 having a Y geometry 34 in the illustration in accordance with FIG. 7 comprises the first web 36, the second web 38 and the third web 40. The first web 36 and the second web 38 delimit a first holding compartment 174 in which the at least one working electrode 16 is held. The at least one working electrode 16 has a coating with a reagent medium 86 of a reagent for detecting the analyte in the body tissue or in the body fluid. It emerges from the illustration in accordance with FIG. 7 that the immobilization medium 142 can be applied to this reagent medium 86. In the design variant, illustrated in FIG. 7, of the electrode arrangement 16, 18, 20 of the electrode pack 132, the immobilization medium 142 is applied to the peripheral surface of the at least one working electrode 16, the at least one counter electrode 18 and the at least one reference electrode 20. As described previously in conjunction with FIG. 5, the entire electrode pack 132 exiting from the assembly station 130 in accordance with FIG. 4 can also be coated as a whole with the immobilization medium 142, which then constitutes the embedding material 14 illustrated in FIG. 1.

Furthermore, it is to be gathered from the perspective illustration in accordance with FIG. 7 that in conjunction with the third web 40 of the isolation element 42 the second web 38 delimits a third holding compartment 178 in which, in the exemplary embodiment in accordance with FIG. 7, the at least one reference electrode 20 is held. Finally, the third web 40 and the first web 36 of the isolation element 32 in accordance with the illustration in FIG. 7 delimit a second holding compartment 176, in which the at least one counter electrode 18 of the electrode arrangement 16, 18, 20 is located. It emerges from the illustration in accordance with FIG. 7 that a diameter 170 of the reference electrode is of the order of magnitude of approximately 100 µm, while reference numeral 172 denotes the sum of the diameters of the at least one reference electrode 20, the at least one counter electrode 18 and the material thickness of the third web 40 of the isolation element 32. The line 172 in accordance with the illustration in FIG. 7 has a length of the order of magnitude of approximately 250 µm.

It follows from the said dimensions of the electrode arrangement 16, 18, 20 in accordance with the perspective illustration in FIG. 7 that the proposed electrode arrangement 16, 18, 20 of the inventively proposed electrochemical sensor 10 has very compact dimensions, and this is based on the parallel arrangement of the at least one working electrode 16, the at least one counter electrode 18 and the at least one reference electrode 20 in the holding compartments 174, 176 and 178 of the isolation element 32.

Figure 8:
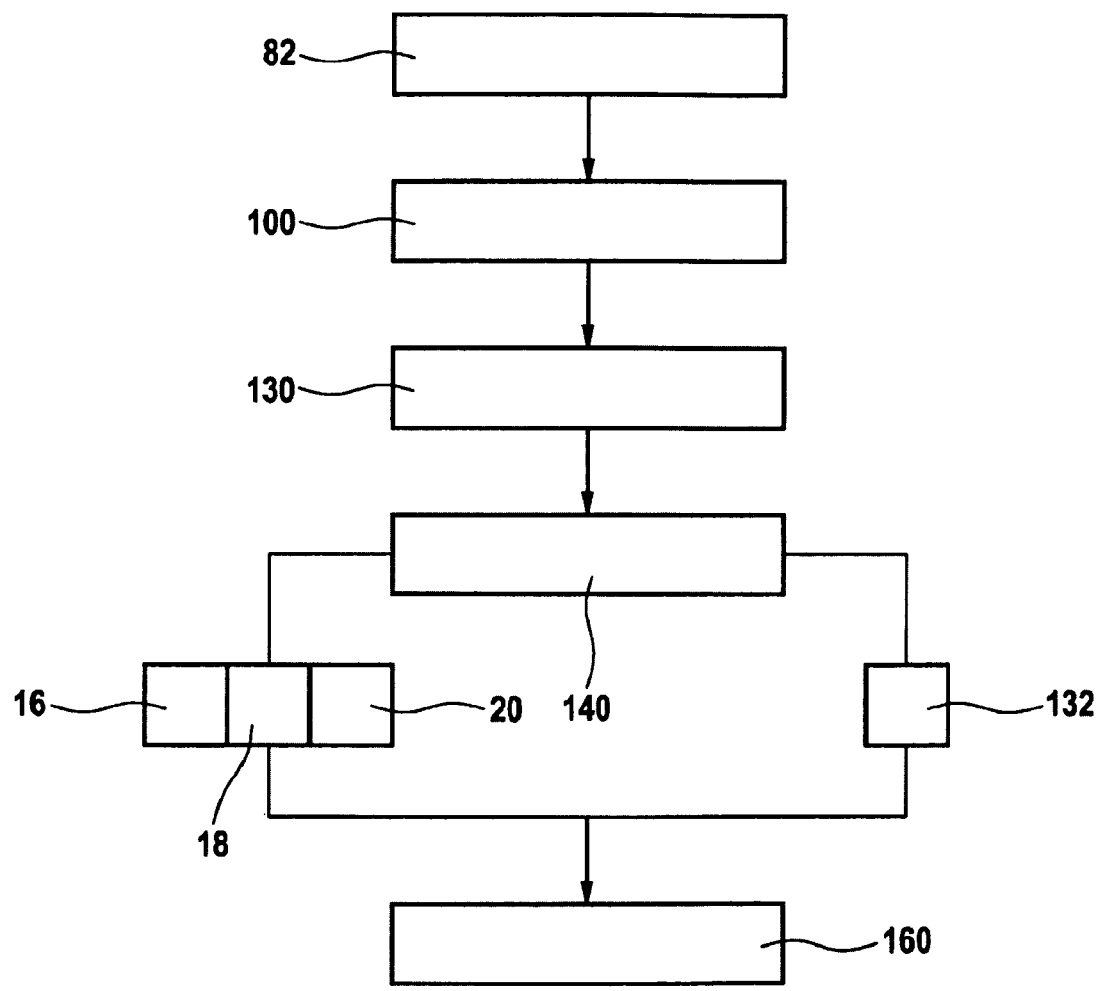
FIG. 8 shows a schematic flowchart of the method.

A schematic illustration of the production method for producing the electrochemical sensor, in particular the electrode arrangement, is to be gathered from the illustration in accordance with FIG. 8.

It follows from the flowchart in accordance with FIG. 8 that in the course of the annular nozzle coating operation 82 the at least one working electrode is coated with the reagent medium 86 which constitutes a reagent suitable for detecting the analyte. The reagent medium 86, which is located downstream of the annular nozzle coating operation 82 on the surface 94 of the at least one working electrode 16, is dried in the subsequent drying step inside the drying station 100. Subsequently, the at least one working electrode 16, now coated with the reagent medium 86 on the surface 94 is assembled with the at least one counter electrode 18, the at least one reference electrode 20, and the isolation element 32, produced in one embodiment by the extrusion method. The assembly is performed in an assembly station 130. The electrode pack 132 obtained from the assembly station 130 is subsequently subjected to an immobilization medium coating operation 140. In the course of the immobilization medium coating operation 140, it is possible to apply the immobilization medium 142 both to the electrode pack 132, obtained in the assembly station 130, as a whole, and consequently to embed said electrode pack in the immobilization medium. In addition, it is also possible to coat the at least one working electrode 16, the at least one counter electrode 18 and the at least one reference electrode 20 separately, and to assemble these coated individual electrodes in the assembly station 130.

Either the coated electrode pack 152 or the assembled individually coated individual electrodes 16, 18, 20 are separated in the course of the cutting to length operation 160 following the immobilization medium coating operation 140. Sections 164 that can be formed in different lengths 162 are produced in the course of the cutting to length operation 160, the length 162 being determined by the particular application of the electrode arrangement for use in an electrochemical sensor 10.

A segment of an electrode surface of a working electrode 16 is shown schematically in FIG. 9 in a sectional illustration. In this example, the working electrode has a gold wire 180. The gold wire 180 is coated with a reagent medium 86 in accordance with the method illustrated in FIG. 8. In this example, the reagent medium is composed of three different components: conductive carbon particles 182, brownstone particles 184, GOD particles and/or GOD conglomerates 186 as well as a binder polymer 188. The binder polymer 188 ensures the processing characteristics of the reagent medium in the undried state. In this case, the viscosity and/or surface tension of the reagent medium 86 is set by choice of the binder polymer 188 such that said polymer can be effectively processed in the "wet" (that is to say undried) state by annular nozzle coating 82, and forms a homogeneous, uniform layer that adheres well to the gold wire 180. At the same time, the binder polymer is selected in such a way that it can be dried at moderate temperatures without, for example, GOD 186 being thermally destroyed in this drying step. Suitable binder polymers 188 are also provided, for example, by mixtures, for example mixtures of polymers with various solvents.

Furthermore, FIG. 9 also illustrates the layer of the immobilization medium 142. The latter surrounds the reagent medium 86 and prevents body fluid (denoted symbolically here by 190) from coming into direct contact with the brownstone particles 184 and with the GOD particles 186, and prevents GOD from diffusing into the body fluid 190. At the same time, oxygen and glucose as analyte to be detected can diffuse from the body fluid 190 through the layer of the immobilization medium 142 and thus reach the reagent medium 86.

Finally, the reaction used to detect glucose 194 in body fluid 190 is illustrated symbolically in FIG. 9 by a "reaction, arrow" 192. The glucose 194 is oxidized via the enzyme GOD 186 to form gluconolacton, and oxygen is subsequently reduced to $H_2O_2$ by the enzyme GOD 186. Subsequently, the $H_2O_2$ is then catalytically oxidized by the brownstone 184, and in the process the electrons are transferred onto the outgoing gold wire 180 via the carbon particles 182 that are in contact with the brownstone 184. The potential of the gold wire 180 (or of the entire working electrode 16), thus influenced, can be detected in the way described above, for example by an amperometric measurement, and it is possible from this to infer the concentration of the glucose in the body fluid 190.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method of producing an electrochemical sensor for determining an analyte concentration in a body tissue or a body fluid, comprising the following steps:
providing at least two electrodes and coating at least one of the at least two electrodes with a reagent medium for detecting the analyte;
assembling a slab-shaped electrode pack by providing an isolation element having a profiled shape and having at least two holding compartments, and extending the at least two electrodes along the isolation element into respective ones of the holding compartments;
subjecting either individual ones of the at least two electrodes or the electrode pack to an immobilization medium coating operation; and
feeding the electrode pack to a cut-to-length operation for separation.

2. The method as claimed in claim 1, further comprising the step of passing the at least one of the two electrodes through a drying station after the step of coating with the reagent medium.

3. The method as claimed in claim 1, wherein one or both of the step of coating with the reagent medium and the step of subjecting to the immobilization medium coating operation are carried out by use of one of an annular nozzle coating method and an electroplating method.

4. The method as claimed in claim 3, wherein the step of coating with the reagent medium comprises use of a first annular nozzle for substantially wetting the surface of the at least one of the at least two electrodes.

5. The method as claimed in claim 3, wherein the step of subjecting to the immobilization medium coating operation comprises use of a second annular nozzle for substantially coating the individual ones of the at least two electrodes or the electrode pack with an immobilization medium.

6. The method as claimed in claim 1, wherein the cut-to-length operation comprises separating individual sections of the electrode pack into application-specific lengths.

* * * * *